United States Patent [19]

Szachowicz et al.

[11] Patent Number: 4,573,460

[45] Date of Patent: Mar. 4, 1986

[54] TALKING TRACHEOSTOMY TUBE

[75] Inventors: Edward H. Szachowicz, St. Louis Park; John Walsh, LaCrescent, both of Minn.

[73] Assignee: Implant Technologies, Minneapolis, Minn.

[21] Appl. No.: 610,417

[22] Filed: May 15, 1984

Related U.S. Application Data

[62] Division of Ser. No. 417,727, Sep. 13, 1982, Pat. No. 4,449,523.

[51] Int. Cl.$^4$ ............................................. A61M 25/00
[52] U.S. Cl. ........................... 128/200.26; 128/207.15
[58] Field of Search ...................... 128/200.26, 207.14, 128/207.15, 207.17, 207.16, 912

[56] References Cited

U.S. PATENT DOCUMENTS

| | | | |
|---|---|---|---|
| 2,210,744 | 8/1940 | Winder | 128/207.15 |
| 3,603,308 | 9/1971 | Spradling et al. | 128/204.25 |
| 3,625,793 | 12/1971 | Sheridan et al. | 128/207.15 |
| 3,653,379 | 4/1972 | Glenn | 128/204.25 |
| 3,693,624 | 9/1972 | Shiley et al. | 128/207.15 |
| 3,889,688 | 6/1975 | Eamkaow | 128/207.15 |
| 4,009,720 | 3/1977 | Crandall | 128/207.15 |
| 4,280,492 | 7/1981 | Latham | 128/207.15 |
| 4,305,392 | 12/1981 | Chester | 128/207.15 |
| 4,315,505 | 2/1982 | Crandall et al. | 128/207.15 |
| 4,327,205 | 5/1982 | Bronson et al. | 128/207.15 |
| 4,459,984 | 7/1984 | Liegner | 128/207.15 |

FOREIGN PATENT DOCUMENTS 1040425  8/1966  United Kingdom ........... 128/207.15

OTHER PUBLICATIONS

Portex, Inc., "Trach Talk Tube", Catalog p. #109.
R. Carrat, "Canule Tracheale Permettant La Phonation Pondant La Ventilation Artificelle Par Tracheotomie", Anesth. Analg., (Par), vol. 16, pp. 597-598, Jun.-Aug. 1959.
Safar et al., "Cuffed Tracheotomy Tube vs. Tank Respirator for Prolonged Artificial Ventilation", Archives of Physical Medicine and Rehabilitation, vol. 20, p. 809. Jan.-Dec. 1963.
Jackson, "New Type of Tube for Tracheotomy with Inflatable Cuff and Inner Cannula," Journal of Neurosurgery, pp. 517-520, Jul.-Aug. 1963.
P. Carrat, "La Phonation au Cours De La Ventilation Pulmonaire Artificelle Par Tracheotomie", *Reverse Lasyne*, Bordeaif, vol. 84, pp. 517-520, Jul.-Aug. 1963.
Hessler et al., "Tracheostomy Cannula for Speaking During Artificial Respiration", Anesthesiology, vol. 25, No. 5, pp. 719-721, Sep.-Oct. 1964.

(List continued on next page.)

*Primary Examiner*—Henry J. Recla

[57] ABSTRACT

A talking tracheostomy tube according to the teachings of the present invention is shown in the preferred embodiment as including an inner cannula removably received within an outer cannula. The tracheostomy tube further includes, in the preferred embodiment, a first cuff for sealing between the outer cannula and the trachea for substantially preventing air introduced through the inner cannula to escape from the trachea through the larynx. In the preferred embodiment, air is introduced into the trachea above the first cuff by ports directionally drilled through the outer cannula and in fluid communication with a secondary passageway formed by and between the inner and outer cannulas. The inner end of the secondary passageway is formed by a sealing obstruction integrally formed in the inside surface of the outer cannula adjacent the inner end for the sealing receipt of the inner cannula. The outer end of the secondary passageway is sealed by a collar integrally formed on the outer end of the inner cannula which abuts and seals within a recess of a collar integrally formed on the outer end of the outer cannula. In its preferred form of the present invention, the tracheostomy tube further includes a second cuff for sealing between the outer cannula and the stoma of the patient for preventing the secondary air introduced through the ports from escaping through the stoma in the neck of the patient.

11 Claims, 8 Drawing Figures

OTHER PUBLICATIONS

Proctor & Sulfar, "Management of Airway Obstruction", *Respiratory Therapy*, F. A. Davis Co., Philadelphia, 1965.

"A Means of Speaking for Patients with Cuffed Tracheostomy Tubes", British Medical Journal, vol. 3, p. 547, Aug. 1967.

Obier, et al., "Enhancing Therapeutic Communication with Acutely Ill Patients", *Heart and Lung*, vol. 2, No. 1, pp. 49-53, Jan.-Feb. 1973.

Lawless, "Helping Patients with Endotracheal and Tracheostomy Tubes Communicate", *American Journal of Nursing*, vol. 75, No. 12, pp. 2151-2153, Dec. 1975.

Hansen et al., "Vocalization via a Cuffed Tracheostomy Tube", *Anesthesia*, vol. 30, pp. 78-79, 1975.

Safar et al., "Speaking Cuffed Tracheostomy Tube", *Critical Care Medicine*, vol. 3, No. 1, pp. 23-26, Jan.-Feb. 1975.

*Japanese Journal of Anesthesiology*, vol. 25, No. 12, pp. 1312-1315, Nov. 1976.

TALKING TRACHEOSTOMY TUBE

This application is a division of application Ser. No. 417,727, filed Sept. 13, 1982, now U.S. Pat. No. 4,449,523.

BACKGROUND

The present invention relates generally to tracheostomy tubes and relates more specifically to talking tracheostomy tubes.

Whenever a patient is placed on a ventilator, it is with an obligate loss of speech. This loss of speech may result in great fear, frustration and withdrawal of the ventilated patient. Many techniques of communication have been substituted for speech in an effort to alleviate anxiety of the patient and to facilitate health care delivery. These substitutes include lip reading, writing and the use of hand signals. Unfortunately, few hospital staff are able to lip read, writing is cumbersome, and many times the ventilated patient lacks the strength or ability to comply as is the case with hand signals. Speech with the electrolarynx has also been used. However the electrolarynx takes some time to master and the paralyzed patient finds its use nearly impossible.

Other methods to communicate with patients ventilated via a tracheostomy have involved laryngeal speech. Laryngeal speech has been accomplished in three ways. First the cuff of the tracheostomy tube has been partially deflated allowing a minimal air leak around the cuff and through the larynx during the lung filling phase of ventilation. Although this technique does result in speech, the speech is intermittent, dependent on the respirator cycle, does not allow measurement of tidal volumes, and may result in aspiration.

Another method of speech is with a valved, fenestrated tracheostomy tube. The tracheostomy tube used may be equipped with a ventilator activated valve that directs air through a fenestration in the tracheostomy tube and through the larynx during the expiratory phase of ventilation. This method, again, is intermittent, dependent on the phase of the respirator, does not allow measurement of air return during speech, may result in aspiration during the expiration phase, and often could only be used with a Bird respirator for which it was designed.

Another method of speech involves attaching a catheter "piggy-back" along the length of a tracheostomy tube nearly to the cuff. This catheter was then connected to an air or oxygen source. With the tracheostomy tube and catheter in place, air or oxygen travels via the catheter through the stoma along the length of the tracheostomy tube. The air or oxygen may then be released into the trachea superior to the cuff where it flows through the larynx and out the pharynx. In addition to the production of laryngeal speech, this technique may be used with any respirator, speech may be uninterrupted, speech may be independent of the respirator phase, exact tidal measurements can be made, there are no moving parts, and finally there is substantially no chance of aspiration during any phase of respiration.

However, prior to the present invention, existing "piggy-back" type tracheostomy tubes have encountered the same difficulties of those in the past. That is, they may produce discomfort at high air flows through the larynx (i.e. greater than 5 liters/minute) which may be necessary to produce speech. In addition, leakage of air around the stoma was encountered as was subcutaneous emphysema.

SUMMARY

The present invention solves these and other problems in tracheostomy tubes by providing a talking tracheostomy tube which introduces air or oxygen above the sealing member between the tracheostomy tube and the trachea.

In the preferred embodiment of the present invention, the tracheostomy tube includes a further sealing member, shown in its most preferred form as an inflatable cuff, for sealing between the tracheostomy tube and the stoma of the neck of the patient for preventing leaks of the air or oxygen introduced for phonating purposes therethrough.

In the preferred embodiment of the present invention, the air or oxygen for phonating purposes is introduced to the trachea by a secondary passageway formed between an inner and an outer cannula. Specifically, the cross section of the inner cannula is complementary to and for receipt into the outer cannula but of a smaller size to create the secondary passageway between the outside surfae of the inner cannula and the inside surface of the outer cannula. The outer and inner ends of the secondary passageway are sealed by sealing between the outer ends and the inner ends of the outer and inner cannulas.

Thus, it is an object of the present invention to provide a novel talking tracheostomy tube.

It is further an object of the present invention to provide such a novel talking tracheostomy tube which provides a source of air to the larynx of the patient which is separate and independent from the ventilator.

It is further an object of the present invention to provide such a novel talking tracheostomy tube which minimizes or eliminates discomfort created by high air flows directed into the trachea towards the larynx.

It is further an object of the present invention to provide such a novel talking tracheostomy tube which prevents air leaks through the stoma and reduces the chances of subcutaneous emphysema in recent tracheostomys.

It is further an object of the present invention to provide such a novel talking tracheostomy tube which is easy to clean and routinely maintain.

It is further an object of the present invention to provide such a novel talking tracheostomy tube wherein the passageway for the phonating air or oxygen is formed internally of the tracheostomy tube and does not require components which are consuming in time, labor, or material to manufacture or assemble.

It is further an object of the present invention to provide such a novel talking tracheostomy tube which maximizes material, is simple in design, and is easy to manufacture and assemble.

These and further objects and advantages of the present invention will become clearer in the light of the following detailed description of an illustrative embodiment of this invention described in connection with the drawings.

DESCRIPTION OF THE DRAWINGS

The illustrative embodiment may best be described by reference to the accompanying drawings where.

Figure 2:
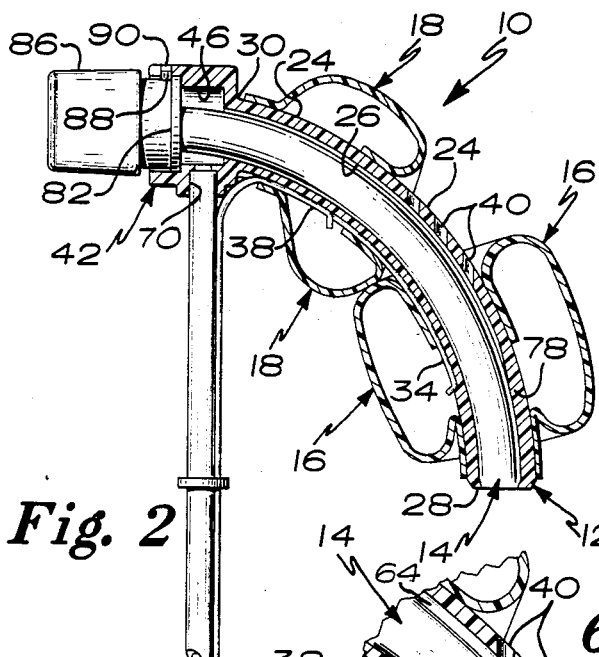
FIG. 2 shows a partial cross sectional view of the talking tracheostomy tube of FIG. 1.

All figures are drawn for ease of explanation of the basic teachings of the present invention only; the extensions of the figures with respect to number, position, relationship, and dimensions of the parts to form the preferred embodiment will be explained.

Where used in the various figures of the drawings, the same numerals designate the same or similar parts in the talking tracheostomy tube. Furthermore, when the terms "first", "second", "upper", "inner", "outer", "outside", "inside", and similar terms are used herein, it should be understood that these terms have reference only to the structure shown in the drawings as it would appear to a person viewing the drawings and are utilized only to facilitate describing the present invention.

DESCRIPTION

A talking or speaking tracheostomy tube according to the teachings of the present invention is shown in the Figures and generally designated 10. Tube 10 in a preferred form generally includes an outer cannula 12, an inner cannula 14, a first sealing member shown in its most preferred form as an inflatable low pressure cuff 16, a second sealing member shown in its most preferred form as an inflatable low pressure cuff 18, and a neck flange 20.

In a preferred embodiment of the present invention, outer cannula 12 is arcuate in shape and formed of a semi-rigid, thin walled tube having an outside surface 24, an inside surface 26, a first, inner end 28, and a second, outer end 30. Cuff 16 is attached to outside surface 24 of outer cannula 12 in a sealed manner adjacent end 28. For inflating cuff 16, a pilot balloon assembly 32 and filling tube 34 are provided in the preferred embodiment of the present invention. Filling tube 34 is in air communication between assembly 32 and cuff 16. Assembly 32 includes an inflatable bladder and check valve assembly actuated by a hypodermic syringe. As is well known in the art, cuff 16 may be inflated or deflated utilizing a hypodermic syringe, not shown, for pressurizing or depressurizing assembly 32. It should then be noted that filling tube 34 may be imbedded in the wall of outer cannula 12 so that no obstructions are presented on outside surface 24 of cannula 12, if desired.

Cuff 18 is attached to outside surface 24 of outer cannula 12 in a sealed manner in a spaced relation from cuff 16 and end 30. For inflating cuff 18, a pilot balloon assembly 36 and a filling tube 38 are provided in the preferred embodiment of the present invention. Filling tube 38 is in air communication between assembly 36 and cuff 18. As is well known in the art, cuff 18 may be inflated and deflated utilizing a hypodermic syringe, not shown, for pressurizing or depressurizing assembly 36. It should then be noted that filling tube 38 may be imbedded in the wall of outer cannula 12 so that no obstructions are presented on outside surface 24 of cannula 12, if desired.

Located immediately superior to cuff 16, tube 10 further include in the preferred embodiment of the present invention an array of air exit ports 40 extending through the upper wall of cannula 12. In its most preferred form, the array includes eight ports 40 placed in an area 1.4 centimeters by 0.7 centimeters. In the preferred embodiment, ports 40 have diameters of 1.5 millimeters and are directionally drilled and in the most preferred form are along an axis which is generally parallel to a tangent of the curved shape of cannula 12.

In the preferred embodiment of the present invention, collar 42 is integrally formed on end 30 of cannula 12. Collar 42 in its most preferred form includes an outer axially extending internal inner recess 44 terminating in an axially extending internal inner recess 46 having a lesser diameter forming an abutment shoulder 48 therebetween. In its most preferred form, neck flange 20 is integrally formed on collar 42. In the preferred embodiment of the present invention, tube 10 may be secured to the neck of a patient by abutting flange 20 against the neck of the patient when tube 10 is inserted into the trachea and a neck strap 50 may be passed around the neck of the patient and having its ends secured to the opposite ends of flange 20.

Figures 4, 8:
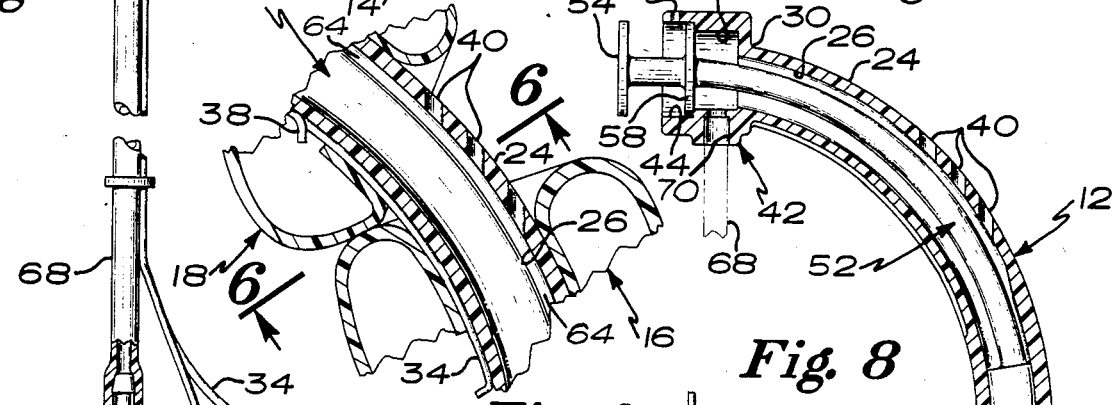
FIG. 4 shows an enlarged, partial cross sectional view of the talking tracheostomy tube of FIG. 1.
FIG. 8 shows a partial cross sectional view of the talking tracheostomy tube of FIG. 1.
Figure 3:
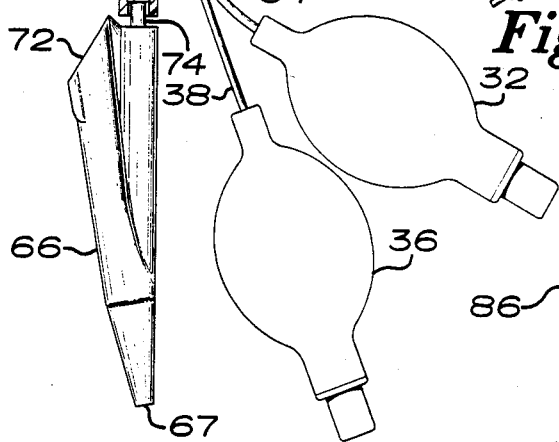
FIG. 3 shows an exploded, partial cross sectional view of the talking tracheostomy tube of FIG. 1.
Figure 7:
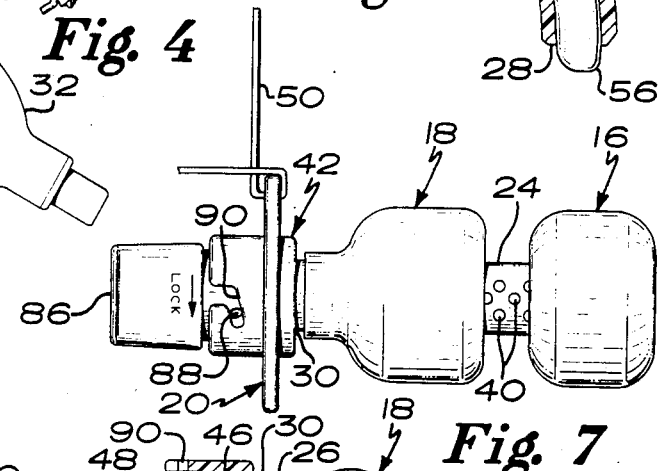
FIG. 7 shows a top view of the talking tracheostomy tube of FIG. 1.

For insertion of cannula 12, an obturator 52 is provided in the preferred embodiment of the present invention as best seen in FIG. 8. Obturator 52 is arcuate in shape and complementary to the shape of and for receipt into inside surface 26 of cannula 12. In its preferred form, obturator 52 includes a first, handle end 54, a second, enlarged rounded end 56 and has a length slightly longer than cannula 12 such that end 56 extends slightly past end 28 of cannula 12. In its most preferred form, end 56 has a cross section which is complementary to the cross section of cannula 12 adjacent end 28 and has a size substantially equal to and for slidable receipt within inside surface 26 of cannula 12 adjacent end 28. Obturator 52 further includes in its most preferred form an abutment plate 58 spaced from end 54 for abutment with shoulder 48 of collar 42 to prevent further insertion of obturator 52 and to allow ease of removal of obturator 52 from outer cannula 12. End 28 may be rounded in a complementary manner to end 56 of obturator 52. Thus, the inner end of tube 10 having obturator 52 inserted presents a smooth insertion surface formed by end 56 of obturator 52 and end 28 of cannula 12.

Figure 1:
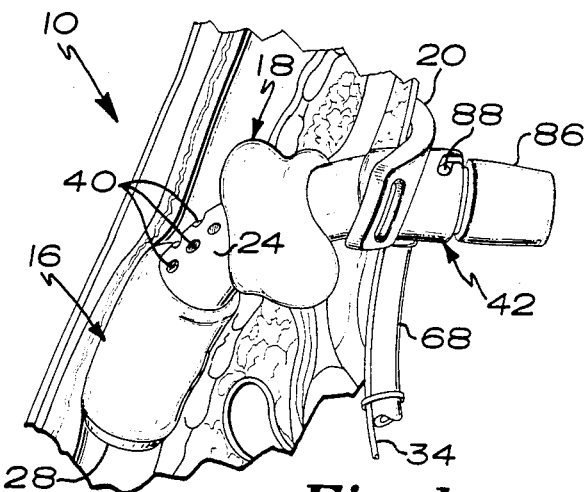
FIG. 1 shows a talking tracheostomy tube according to the teachings of the present invention as it may be located in the neck of a patient.

With cuffs 16 and 18 deflated and with obturator 52 located within cannula 12 as best seen in FIG. 8, cannula 12 may be inserted in the incision of the neck of the patient and into the trachea until flange 20 abuts with the neck of the patient. Strap 50 may then be attached and obturator 52 removed. Cuff 16 may then be pressurized in the manner set forth hereinbefore for generally sealing cannula 12 with the trachea as best seen in FIG. 1. When desired, cuff 18 may be pressurized in the manner set forth hereinbefore for generally sealing cannula 12 with the stoma of the patient as best seen in FIG. 1.

Figures 5, 6:
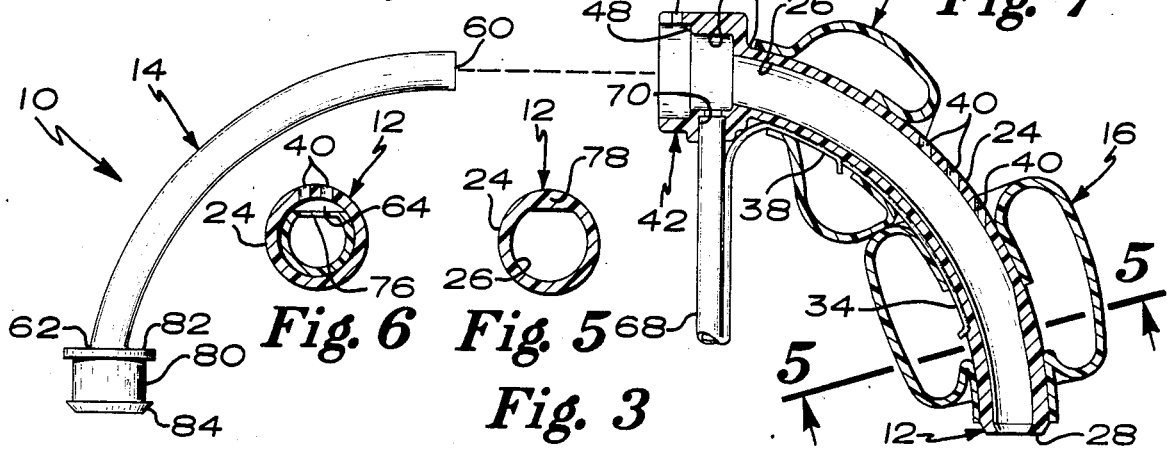
FIG. 5 shows a cross sectional view of the talking tracheostomy tube of FIG. 1 according to section line 5—5 of FIG. 3.
FIG. 6 shows a cross sectional view of the talking tracheostomy tube of FIG. 1 according to section line 6—6 of FIG. 4.

In the preferred embodiment of the present invention, inner cannula 14 is formed of a semi-rigid, thin walled tube having a first end 60 and a second end 62. Inner cannula 14 is arcuate in shape and complementary to and for receipt into inside surface 26 of outer cannula 12. The diameter of cannula 14 is approximately equal to the diameter of inside surface 26 of outer cannula 12. However, as best seen in FIG. 6, in its most preferred form cannula 14 has a truncated circular cross section. Specifically, in its most preferred form, cannula 14 includes a flat surface 76 which extends along a chord of the circular cross section of cannula 14. An air passageway 64 is formed between surface 76 of inner cannula 14 and inside surface 26 of outer cannula 12 in the preferred embodiment of the present invention.

Air communication is provided to passageway 64 in the preferred embodiment of the present invention by an air control valve or suction catheter 66, such as by a thumb valve shown, having an inlet 67 in fluid communication with a source of pressurized air or oxygen, not shown, and an air line 68. In the most preferred form, an air inlet 70 is formed in collar 42 in fluid communication with inner recess 46 which in turn is in fluid commuication with passageway 64. Air ports 40 are further in communication with passageway 64. Valve 66 includes a first outlet 72 and a second outlet 74. Air line 64 is in fluid communication with inlet 70 and outlet 74. Thus, pressurized air or oxygen may be supplied through ports 40 when outlet 72 is blocked such as by the thumb of a person. When it is not necessary to supply air or oxygen through ports 40, outlet 72 is not blocked allowing the air or oxygen to freely escape to the environment through outlet 72.

In the preferred embodiment of the present invention for providing a sealed inner end of passageway 64, inside surface 26 of outer cannula 12 is formed with a sealing obstruction 78 adjacent end 28 as best seen in FIG. 5. Specifically, the cross section of cannula 12 through obstruction 78 is complementary to and for the sealing receipt of the cross section of cannula 14. Thus, a sealing relationship may be formed between end 28 of cannula 12 and end 60 of cannula 14 when cannula 14 is located within cannula 12.

Tube 10 in the preferred embodiment of the present invention includes a collar 80 integrally formed on end 62 of inner cannula 14. In its most preferred form, collar 80 includes an integral abutment washer or plate 82 for sealing engagment with shoulder 48 of collar 42. Thus, washer 82 and shoulder 48 of collar 42 provides a sealed outer end of passageway 64. Collar 80 further includes a male snap connector 84 in its most preferred form.

Tube 10 further includes in the preferred embodiment of the present invention a connector 86 for possible connection to a line, not shown, of pressurized air or oxygen for supplying air or oxygen for communication through cannula 14, through the trachea, to the lungs of patient. Connector 86 includes in its most preferred form a female snap connector for releasable sealing with connector 84 of collar 80 of cannula 14.

In the preferred embodiment of the present invention, at least one pin 88 is formed on connector 86 of cannula 14 for locking receipt into complementary slots 90 formed in collar 42 of cannula 12 for locking cannula 14 within cannula 12. In its most preferred form, slot 90 is L-shaped such that for insertion and locking of cannula 14 into cannula 12, it is necessary to first push cannula 14 into cannula 12 and then to twist or turn cannula 14 in cannula 12 such that pin 88 travels along the leg of slot 90 and then is twisted into the other leg of slot 90. Thus, the locking mechanism of the present invention insures a sealing engagement of washer 82 of collar 80 with shoulder 48 of collar 42 and of end 60 of cannula 14 with end 28 of cannula 12.

Now that the construction of tube 10 of the present invention has been explained, subtle features and advantages of the present invention can be set forth and appreciated. With cuff 16 inflated in the tracheostomy of the patient, tracheostomy tube 10 of the present invention functions in a similar manner as prior tracheostomy tubes; however, tracheostomy tube 10 according to the teachings of the present invention obtains advantages over prior tracheostomy tubes and further allows the patient to talk, when desired. Specifically, cuff 18 may be inflated utilizing balloon assembly 36 as set forth hereinbefore. Cuff 18 seals off any reflux of air around tracheostomy tube 10 through the stoma of the patient. Valve 66 may be actuated, for example by placing a thumb over outlet 72, such that pressurized air or oxygen is supplied through passageway 64 and through ports 40 formed in outer cannula 12. Air released through ports 40 is directed upwardly into the trachea and toward the larynx of the patient such that the patient is free to phonate and communicate at will. It is recommended that cuff 18 should be deflated and not be inflated when it is not desired to utilize tube 10 in a talking function to avoid possible irritation or discomfort.

If air is directed towards the walls of the trachea or at a large velocity, discomfort may be produced. Ports 40 in the preferred embodiment are directionally drilled to specifically direct the airstream upwards in the trachea toward the larynx and away from and not at the back wall of the trachea. Furthermore, the large numbers of ports 40 in the array baffle the airstream, reduce its velocity, diffuse delivery, and allow a more natural air column to stream upwards towards the larynx. Additionally, the large number and area of ports 40 also avoids problems of blockage by secretions if only a single port would have been provided. Therefore, tube 10 according to the teachings of the present invention alleviates discomfort to the patient which occurred in prior talking tracheostomy tubes and does not require additional components such as air skirts. In fact, tube 10 of the present invention may be utilized at high flow rates (i.e. greater than 5 liters per minute) through ports 40. In the preferred embodiment of the present invention, a flow rate of 6 to 8 liters per minute through ports 40 is recommended. At flow rates below this, the rate and volume of speech may be unsatisfactory; while higher flow rates may cause drying of tracheal mucosa.

In the preferred embodiment of the present invention, cuff 18 prevents leakage of air around tracheostomy tube 10 through the stoma and thus insures that air introduced to the trachea through ports 40 travel to the larynx for vocalization purposes and does not merely escape from the trachea as was common in prior talking tracheostomy tubes. Further, unnecessary stomal emission and subcutaneous emphysema may be prevented utilizing cuff 18 of the present invention.

It should further be appreciated that a separate source of air or oxygen from the normal ventilating source of air flowing through inner cannula 14 is provided in the preferred embodiment by utilizing valve 66, line 68, passageway 64 and ports 40. Thus, talking by a patient utilizing tracheostomy tube according to the present invention is not intermittent, is not dependent on the phase of the respirator, does not in any way interfere with the ventilation of the patient through inner cannula 14 such as to cause aspiration, and does not interfere with the measurement of air return during speech. Furthermore, tracheostomy tube 10 according to the teachings of the present invention has no moving parts and thus is not prone to mechanical failures such as the failure of valves as was common in valve fenestrated tracheostomy tubes.

Thus, utilizing tube 10 according to the teachings of the present invention provides a flow of air or oxygen to the larynx so that the patient can vocalize words in the usual manner, producing a natural sounding laryngeal speech complete with the patient's own tonal qualities.

Furthermore, in addition to the advantages of laryngeal speech obtained by the present invention, some of which have been set forth hereinbefore, tracheostomy tubes according to the teachings of the present invention obtain many other advantages over existing tracheostomy tubes of either the talking or non-talking type. For example, forming the cannula of tube 10 by an outer cannula 12 and an inner cannula 14 has several advantages. Specifically, it is not necessary to remove the entire tube 10 for clearing dried secretions from tube 10, but rather it is only necessary to remove inner cannula 14 while outer cannula 12 remains in position. Thus, it is not necessary to reinsert outer cannula 12 whenever it is necessary to clear or otherwise provide routine care to tracheostomy tube 10. Furthermore, it should be noted that cannula 14 does not in any way interfere with the ventilation of the patient utilizing tube 10 of the present invention.

It should be noted that forming passageway 64 between inner cannula 14 and outer cannula 12 obtains several advantages. For example, the number of components are reduced and thus the steps of assembly are also less. The outer insertion surface of tube 10 does not include any interfering or protruding objects which could interfere with insertion of tube 10 or produce discomfort with tube 10 in place since passageway 64 is located internally of tube 10. Furthermore, it is not necessary to have passageway 64 formed integrally in cannula 12 or cannula 14 which would make their manufacture more expensive. Thus, the preferred form of the present invention obtains several advantages.

It can then also be appreciated that tracheostomy tube 10 of the preferred embodiment of the present invention is easy to manufacture and assemble, and lends itself to mass production techniques.

Now that the basic teachings of the present invention have been explained, many extensions and variations will be obvious to others having ordinary skill in the art. For example, many of the constructional features of the present invention have and obtain advantages over existing tracheostomy tubes. However, the substitution of equivalent or similar structure will be well-known to a person skilled in the art after the teachings of the present invention become known. For example, the structure utilized for locking inner cannula 14 in outer cannula 12 as shown and described can be accomplished by other structure and means which may become known to persons skilled in the art after the present invention becomes known.

Although the sealing members are shown in its preferred forms as cuffs 16 and 18 and cuffs 16 and 18 are inflated by utilizing assemblies 32 and 36 and tubes 34 and 38, respectively, other forms and constructions of sealing members and/or inflation and deflation methods can be utilized after the teachings of the present invention become known.

Additionally, although the manner and method of sealing between the inner and outer ends of the inner and outer cannulas are preferred and believed to be advantageous over the art, other manners and methods of sealing may become known after the teachings of the present invention become known.

Likewise, the particular structure shown in the preferred embodiment of the present invention for providing air to inner cannula 14 and to passageway 64 is believed to be advantageous but other structures and methods will be within the skill of the art after the teachings of the present invention become known.

Although insertion of tube 10 is shown utilizing obturator 54, other forms and methods of insertion can be utilized according to the teachings of the present invention.

Thus since the invention disclosed herein may be embodied in other specific forms without departing from the spirit or the general characteristics thereof, some of which forms have been indicated, the embodiments described herein are to be considered in all respects illustrative and not restrictive. The scope of the invention is indicated by the appended claims rather than by the foregoing description, and all changes which come within the meaning and range of equivalency of the claims are intended to be embraced therein.

What is claimed is:

1. In a tube for insertion into the trachea of a patient to support breathing through a tube passageway having a first end for placement within the trachea below the larynx for directing air or oxygen towards the lungs of the patient and a second end located outside of the trachea and the patient for receiving air or oxygen, and first means for sealing between the tube and the trachea below the larynx for substantially preventing air or oxygen from escaping from the first end of the tube upward in the trachea towards the larynx, with the tube including a wall having an outside surface, and an inside surface, a cannula having said tube passageway located within the tube, with the improvement comprising means for allowing the patient to phonate comprising, in combination: a secondary passageway located within the tube; second means adjacent the second end of said tube for introducing air or oxygen to the secondary passageway; and at least one port formed through the wall of the tube above the first sealing means in fluid communication with the secondary passageway for introducing air or oxygen above the first sealing means into the trachea for movement towards the larynx of the patient, wherein the secondary passageway is defined by said cannula having a cross section that is generally circular in shape but having a flat surface along a chord of the circular cross section that extends the length of said cannula, whereby the secondary passageway is formed between the inside surface of the tube and the flat surface of the cannula, and wherein the tube includes means adjacent the first end thereof for preventing air or oxygen from escaping the secondary passageway below the first sealing means.

2. The tube of claim 1 for insertion through a stoma in the neck of the patient, and wherein the tube further comprises, in combination: third means comprising an annular member positioned on said tube such as to be located within the annular space between the tube and the stoma of the patient for sealing between the tube and the stoma of the patient for preventing the air or oxygen introduced into the trachea through the port from escaping through the stoma in the neck of the patient around the tube.

3. The tube of claim 2 wherein the third means comprises, in combination: a low pressure, inflatable cuff attached to the tube in a sealed manner; and fourth means for inflating the cuff to abut and seal with the stoma of the patient and for deflating the cuff to allow the cuff to generally assume the shape of the tube for introduction of the tube into the stoma of the neck of the patient.

4. The tube of claim 3 wherein the fourth means comprises, in combination: a pilot balloon assembly and a filling tube in fluid communication with the cuff and the balloon assembly wherein air can be introduced or removed from the pilot balloon assembly by a hypodermic syringe for inflating and deflating the cuff.

5. The tube of claim 1 wherein the port is directionally formed in the wall of the tube to direct the air upwards in the trachea towards the larynx and away from the walls of the trachea.

6. The tube of claim 1 including an array of ports to baffle and reduce the velocity of the air or oxygen introduced in the trachea above the first sealing means to allow a more natural flow of the air or oxygen to the larynx of the patient.

7. The tube of claim 1 wherein the cannula includes an outer end and an inside surface; and wherein the tube further comprises, in combination: means for sealing the outside surface of the cannula and the inside surface of the tube adjacent the outer end of the cannula and the second end of the tube.

8. The tube of claim 7 wherein the sealing means adjacent the outer end of the cannula and the second end of the tube comprises, in combination: a collar formed on the second end of the tube having at least one internal recess defining an abutment and sealing shoulder; and a collar formed on the outer end of the cannula for receipt in the internal recess of the tube and having an abutment and sealing surface for abutting and sealing with the abutment and sealing shoulder of the tube.

9. The tube of claim 8 further comprising, in combination: means for locking the cannula with the tube comprising a locking slot formed in the collar of the tube; and a pin operatively attached to the cannula for locking receipt in the locking slot of the tube.

10. The tube of claim 1 wherein the means for preventing air or oxygen from escaping the secondary passageway below the first sealing means comprises, in combination: a sealing obstruction formed integrally with the inside surface of the tube adjacent the first end for shaping the cross section of the tube to be complementary to and for the sealing receipt of the cannula.

11. The tube of claim 1 wherein the means for introducing air or oxygen to the secondary passageway comprises, in combination: a suction catheter including an inlet in fluid communication with a source of pressurized air or oxygen, a first outlet open to the environment, and a second outlet; and means for providing fluid communication between the secondary passageway and the second outlet of the suction catheter.

* * * * *